United States Patent [19]

D'Silva

[11] Patent Number: 4,568,671
[45] Date of Patent: Feb. 4, 1986

[54] PESTICIDAL OXIME N-ALKYL-N-α-(ALKYLTHIO-PHOSPHORO-THIO)ACYL CARBAMATES

[75] Inventor: Themistocles D. J. D'Silva, Chapel Hill, N.C.

[73] Assignee: Union Carbide Corporation, Danbury, Conn.

[21] Appl. No.: 509,451

[22] Filed: Jun. 30, 1983

[51] Int. Cl.[4] ............... A01N 57/12; A01N 57/14; A01N 57/16; C07F 9/165
[52] U.S. Cl. .................. 514/119; 514/112; 514/97; 514/98; 514/92; 514/90; 260/938; 544/57; 548/119; 548/112; 549/5; 549/6; 549/7
[58] Field of Search ............ 260/938; 514/112, 119

[56] References Cited

U.S. PATENT DOCUMENTS 3,733,406  5/1973  Haubein .................... 424/211
4,339,444  7/1982  D'Silva et al. .............. 424/202

FOREIGN PATENT DOCUMENTS 1232930  5/1971  United Kingdom .......... 424/202

Primary Examiner—Robert T. Bond
Attorney, Agent, or Firm—Gerald L. Coon

[57] ABSTRACT

Oxime N-alkyl-N-α-(alkylthio-phosphorothio)acyl carbamates represented the structure:

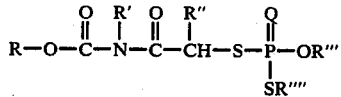

wherein the R represents various imino radicals, Q is oxygen or sulfur and the numbered R groups represent various alkyl substituents, which exhibit superior insecticidal and miticidal activity.

18 Claims, No Drawings

PESTICIDAL OXIME N-ALKYL-N-α-(ALKYLTHIO-PHOSPHOROTHIO)ACYL CARBAMATES

FIELD OF THE INVENTION

The present invention relates to certain phosphorylated oxime carbamates useful as pesticides. More particularly, the present invention relates to oxime N-alkyl-N-α-(alkylthiophosphorothio)acylcarbamates useful as the active agents in insecticidal and miticidal compositions for controlling insects and mites.

BACKGROUND OF THE INVENTION

U.S. Pat. No. 4,339,444 (D'Silva. et al.) discloses the preparation and use of pesticidal acyclic and heterocyclic oximino phosphorothioates. British Pat. No. 1,232,930 discloses pesticidal oxime N-acyl carbamates wherein the acyl group is alkyl, halogen substituted alkyl or aryl such as benzoyl.

U.S. Pat. No. 3,600,471 (Haubein I) and U.S. Pat. No. 3,733,406 (Haubein II) disclose N-α-dialkoxyphosphinothiocetyl-N-methylcarbamates of phenols having insecticidal and acaricidal activity. Such compounds exhibit only moderate pesticidal activity and undesirably high mammalian toxicity.

It was reported by J.J.K. Boulton, et al., in the journal *Pesticide Science*, Vol. 2, pp. 10–15 (1971), that N-acylation of oxime carbamates results in an almost total loss of toxicity of these compounds with respect to both insects and mammals.

SUMMARY OF THE INVENTION

The present invention is directed to oxime N-alkyl-N-α-(alkylthio-phosphorothio)acylcarbamates which are useful as insecticides and miticides.

The invention is also directed to a process for manufacturing such compounds, insecticidial and miticidal compositions comprising an acceptable carrier and a pesticidally effective amount of such compounds, and methods for controlling insects and mites using such compounds.

DETAILED DESCRIPTION OF THE INVENTION

The oxime carbamates of this invention have the general structure:

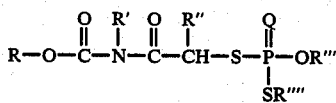

wherein:
Q is oxygen or sulfur;
R' is $C_{1-4}$ alkyl;
R" is hydrogen or $C_{1-4}$ alkyl;
R''' and R'''' individually $C_{1-6}$ alkyl; and
R is:

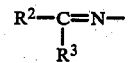

or

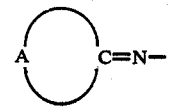

wherein:
$R^2$ is (a) alkyl, cycloalkyl, or phenyl all of which may be optionally substituted with one or more halogen, alkylsulfinyl, alkylsulfonyl, amido, alkythio, alkoxy, cyano or nitro groups; or (b) alkanoyl, alkoxy, alkylthio, aminocarbonyl, alkylaminocarbonyl or dialkylaminocarbonyl, provided that $R^2$ may contain no more than six aliphatic carbon atoms;
$R^3$ is (a) alkyl, alkylthio or alkoxy, all of which may be optionally substituted with cyano, or (b) hydrogen, alkenylthio, alkynylthio, alkoxy or alkoximinoalkyl, provided that $R^3$ may contain no more than six carbon atoms; and
A is a saturated or unsaturated, four or five membered divalent hydrocarbon chain composed of carbon atoms and not more than two atoms selected from the group comprised of oxygen, sulfur and nitrogen atoms wherein said carbon and nitrogen atoms may be substituted with alkyl groups having not more than four carbon atoms.

The acyclic compounds of the present invention include compounds wherein $R^2$ and $R^3$ may be a variety of hydrocarbon radicals which may be branched or straight chain, substituted or unsubstituted, and saturated or unsaturated. If $R^2$ and $R^3$ are different, then the oxime carbamates defined by the above formula can exist in two stereoisomeric forms, E and Z. This invention encompasses both stereoisomeric forms of the oxime carbamates defined by the above formula.

The cyclic compounds are those in which A forms cyclic radicals such as
2-ylidine-1,4-dithiane; 2-ylidine-1,3-dithiane;
4-ylidine-1,3-dithiolane; 2-ylidine-1,3-dithiolane;
2-dicyanomethylidene-4-ylidine-1,3-dithiolane;
2-ylidinethiophane; 4-ylidine-1,3-oxathiolane;
5-ylidine-1,3-thiazolidin-4-one;
2-ylidine-1,3-thiazolidin-4-one;
2-ylidine-tetrahydro-1,4-thiazine;
2-ylidine-4-thiono-1,3-thiazolidin;
2-ylidine-tetrahydro-1,4-thiazin-5-one;
2-ylidine-1,3-thiazolin; and
2-ylidine-1,3,5-trithiane, all of which may have $C_{1-4}$ alkyl substituents. The term "2-ylidine-", for example, denotes that the doubly bonded nitrogen of the oxime portion of the molecule is bonded to the carbon atom at the number 2 ring position in accordance with accepted heterocyclic nomenclature used by those skilled in the art.

Preferred compounds are those in which R' is methyl, R" is hydrogen, R''' is ethyl, R'''' is n-propyl and Q is oxygen. Preferred acyclic compounds are those wherein $R^2$ is alkyl, especially alkyl substituted with alkylthio, alkylsulfonyl, or cyano, and those wherein $R^2$ is aminocarbonyl; and wherein $R^3$ is alkylthio, alkoxy or alkoximinoalkyl such as methoximinoethyl. Preferred cyclic compounds are those wherein A is a five membered chain with two sulfur atoms as ring members such as a 1,4-dithianyl ring and those wherein A is a four membered chain with a sulfur atom as one chain member and a second hetero atom as another chain member such as a 1,3-oxathiolanyl ring or a 1,3-thiazolidinone ring.

The phosphorylated carbamates of the present invention can be prepared using well established procedures for preparing carbamate derivatives. The preferred embodiment is outlined below:

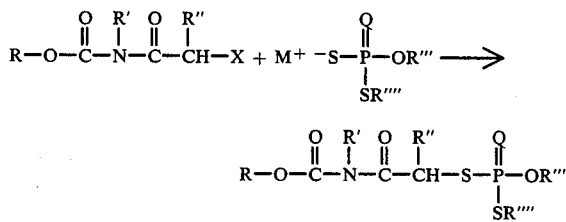

wherein Q, R and R' through R'''' are as previously defined; X is a reactive halogen such as fluorine, chlorine or bromine; and M+ is a cation, such as potassium or ammonium, which forms an ionic bond with phosphorothioate anions.

To prepare the phosphorylated carbamates of this invention, approximately stoichiometrically equivalent amounts of oxime α-haloacylcarbamate and phosphorothioate salt are reacted in a solvent which is inert under the reaction conditions utilized. Illustrative of such suitable solvents are aromatic hydrocarbons such as toluene, xylene, naphthalene, tetralin; aliphatic chlorinated hydrocarbons such as methylene chloride, chloroform, carbontetrachloride, mono-, di- and tri-chloroethylene; low boiling aliphatic ketones and nitriles such as acetone, methylisobutyl ketone, methylethyl ketone, acetonitrile, propionitrile; and ethers such as diethylether, tertiary butylmethyl ether, dioxane and tetrahydrofuran.

The reaction can be conducted at ambient temperature and pressure or over a wide range of temperatures and pressures. Temperatures of between about −20° to about 100° C., and atmospheric pressures are preferred. The reaction is usually conducted under an inert atmosphere, such as nitrogen, with stirring, for a time sufficient to allow the reaction to proceed to completion.

The phosphorothioate salt reactants are known materials which can be prepared by conventional methods known to those skilled in the art, such as the methods in U.S. Pat. No. 4,192,831 to Kiehs, et al. The oxime carbamates can be prepared by a variety of methods.

The oxime α-haloacylcarbamates can be obtained from the reaction outlined below:

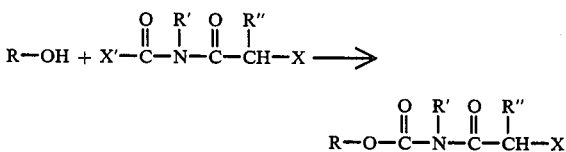

wherein X' is a reactive halogen such as fluorine or chlorine; and X, R, R', and R'' are as defined previously. Equimolar amounts of oxime and N-alkyl-N-haloacyl-carbamoyl halide are mixed in the presence of an acid acceptor such as sodium hydroxide or triethylamine. This procedure is more particularly described in my copending application U.S. Ser. No. 509,452 entitled "Pesticidal Oxime N-Alkyl-N-α-Haloacylcarbamates", filed June 30, 1983.

The N-alkyl-N-α-haloacylcarbamoyl halides are prepared by reacting an alkyl isocyanate. R—N=C=O, with an α-haloacyl halide, X'—C(=O)—CHR'—X, in the presence of a modified anhydrous zinc chloride catalyst. Reagent grade zinc chloride is premixed with silica gel and heated to above about 300° C. This modified zinc chloride catalyst should be stored in an anhydrous atmosphere and used under anhydrous conditions. This procedure is more particularly described in U.S. Pat. application Ser. No. 533,725, filed Sept. 19, 1983.

Illustrative of my invention are the following compounds:

2-methyl-2-nitropropionaldoxime N-(ethoxy-S-propyl-phosphorothioacetyl)-N-methylcarbamate;

4-cyano-2,2-dimethylbutyraldoxime N-(ethoxy-S-propyl-phosphorothioacetyl)-N-methylcarbamate;

2-methoxy-2-methylpropionaldoxime N-(ethoxy-S-propyl-phosphorothioacetyl)-N-methylcarbamate;

1-methylthio-2-methoxy acetaldoxime N-(ethoxy-S-propyl-phosphorothioacetyl)-N-methylcarbamate;

1-methylthio-3,3-dimethyl-2-butanoneoxime N-(ethoxy-S-propyl-phosphorothioacetyl)-N-methylcarbamate;

3-methylsulfonyl-2-butanoneoxime N-(ethoxy-S-propyl-phosphorothioacetyl)-N-methylcarbamate;

3-methylthio-2-butanoneoxime N-(ethoxy-S-propyl-phosphorothioacetyl)-N-methylcarbamate;

2,2-bismethylthiopropionaldoxime N-(ethoxy-S-propyl-phosphorothioacetyl)-N-methylcarbamate;

1-methoxy acetaldoxime N-(ethoxy-S-propyl phosphorothioacetyl)-N-methylcarbamate;

1-isopropylthioacetaldoxime N-(ethoxy-S-propyl phosphorothioacetyl)-N-methylcarbamate;

1-methylthio-1-acetylformaldoxime N-(ethoxy-S-propyl-phosphorothioacetyl)-N-methylcarbamate;

1-cyclopropylacetaldoxime N-(ethoxy-S-propyl phosphorothioacetyl)-N-methyl-carbamate;

1-methylthio-1-N,N-dimethyl -aminocarbonyl formaldoxime N-(ethoxy-S-propyl-phosphorothioacetyl)-N-methylcarbamate;

3-isopropylthiazolidin-4-one-2-oxime N-(ethoxy-S-propyl-phosphorothioacetyl)-N-methylcarbamate;

5,5-dimethyl-2-dicyanomethylidene-1,3-dithiolane-4-oxime N-(ethoxy-S-propyl-phosphorothioacetyl)-N-methyl-carbamate; thiophane-2-oxime N-(ethoxy-S-propyl-phosphorothioacetyl)-N-methylcarbamate;

1,3,5-trithiane-2-oxime N-(ethoxy-S-propyl-phosphorothioacetyl)-N-methylcarbamate;

1-methylthio-trifluoroacetaldoxime N-(ethoxy-S-propyl-posphorothioacetyl)-N-methylcarbamate;

1-methylthioacetaldoxime N-(ethoxy-S-butyl phosphorothioacetyl)-N-methylcarbamate;

1-methylthio-trifluoroacetaldoxime N-(ethoxy-S-propyl-phosphorothioacetyl)-N-methylcarbamate;

1-ethoxyacetaldoxime N-(ethoxy-S-butyl phosphorothioacetyl)-N-methylcarbamate;

1-methylthioacetaldoxime N-(ethoxy-S-hexyl-phosphorothioacetyl)-N-methylcarbamate;

1-(2-cyanoethylthio)acetaldoxime N-(ethoxy-S-propyl-phosphorothioacetyl)-N-methylcarbamate;

1-propargylthioacetaldoxime N-(ethoxy-S-propyl-phosphorothioacetyl)-N-methylcarbamate;

1-allylthioacetaldoxime N-(ethoxy-S-propyl-phosphorothioacetyl)-N-methyl carbamate;

1-ethylthioacetaldoxime N-(ethoxy-S-propyl-phosphorothioacetyl)-N-methylcarbamate;

1-methylthio-1-phenyl formaldoxime N-(ethoxy-S-propyl-phosphorothioacetyl)-N-methylcarbamate; and 1-methylthioacetaldoxime N-(ethoxy-S-propyl-phosphorothioacetyl)-N-propylcarbamate.

Examples 1-4 are illustrative of the methods of preparing the intermediates and the novel compounds of the present invention.

EXAMPLE 1

Preparation of 1-Methylthioacetaldoxime N-chloroacetyl-N-methylcarbamate

To a solution of 2.0 g (0.011 mol) of N-chloroacetyl-N-methylcarbamoyl chloride in 25 ml of toluene was added with stirring a solution of 1.23 g (0.011 mol) of 1-methylthioacetaldoxime in 25 ml of toluene and 1.1 g (0.011 mol) of triethylamine over a period of 15 minutes. After stirring for an additional 2 hours, the solid product was filtered. The filtered cake was washed with water and hexane and air dried to yield 1.9 g of a white solid having a melting point of 156°-158° C.

$C_7H_{11}ClN_2O_3S$: Calcd: C, 35.31; H, 4.65; N, 11.77
Found: C, 35.12; H, 5.02, N, 12.13

EXAMPLE 2

Preparation of 2-Methyl-2-methylthiopropionaldoxime N-chloroacetyl-N-methylcarbamate To a solution of 5.0 g (0.029 mol) of N-chloroacetyl-N-methylcarbamoyl chloride dissolved in 30 ml of toluene was added slowly with stirring to a mixture of 3.9 g (0.029 mol) of 2-methyl-2-methylthiopropionaldoxime dissolved in 25 ml of toluene and 2.6 g (0.29 mol) of triethylamine. The reaction mixture was stirred at ambient temperature for three days. The salt was removed by filtration and the filtrate was concentrated to yield 6.8 g of light yellow viscous oil which crystallized on standing having a melting point of 32°-33° C.

$C_9H_{15}ClN_2O_3S$: Calcd: C, 40.52, H, 5.67, N, 10.48
Found: C, 40.53; H, 6.05, N, 11.52

EXAMPLE 3

Preparation of 2-Methyl-2-methylthiopropionaldoxime N-(ethoxy-S-propyl-phosphorothioacetyl) N-methylcarbamate A solution of 3.1 g (0.011 mol) of 2-methyl-2-methylthiopropionaldoxime N-chloroacetyl-N-methylcarbamate, 4.2 g (0.017 mol) of dimethyl ammonium O-ethyl-S-propyl phosphorodithioate in 30 ml of acetonitrile was stirred at ambient temperature for 3 days. The solvent was removed under vacuum and diluted with ethyl acetate. The solution was washed with water, dried over magnesium sulfate and concentrated to yield 3.4 g of light brown colored oil.

$C_{14}H_{27}N_2O_5PS_3$: Calcd: C, 39.05; H, 6.32; N, 6.51
Found: C, 37.68; H, 7.16; N, 7.11

EXAMPLE 4

Preparation of 1,4-Dithiane-2-oxime N-(ethoxy-S-propyl-phosphorothioacetyl)-N-methylcarbamate Using the procedure of Example 3, 3.2 g (0.014 mol) of 2-oximino-1,4-dithiane-N-chloroacetyl-N-methylcarbamate and 4.0 g (0.016 mol) of dimethylammonium-O-ethyl-S-propylphosphorodithioate in 50 ml of acetronitrile yielded 3.1 g of the desired product as a yellow oil.

$C_{13}H_{23}N_2O_5PS_4$: Calcd: C, 34.96; H, 5.19; H, 6.27
Found: C, 34.03: H, 5.52; N, 6.10

The following compounds, set out in Table I, were prepared in accordance with the examples set forth above.

TABLE I

ELEMENTAL ANALYSES AND MELTING POINTS OF OXIME N—METHYL-N—(O—ETHYL-S—PROPYL-PHOSPHOROTHIOACETYL)CARBAMATES $$R=N-O-\underset{O}{\overset{O}{\underset{\|}{C}}}-N-\underset{\|}{\overset{CH_3}{\underset{|}{C}}}-CH_2S-\underset{SC_3H_7}{\overset{O}{\underset{\|}{P}}}-OC_2H_5$$

| Structure R | Molecular Formula | Elemental Analysis | | | | | |
|---|---|---|---|---|---|---|---|
| | | Calculated | | | Found | | |
| | | C | H | N | C | H | N |
| 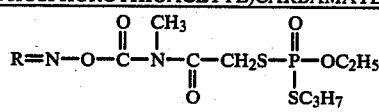CH$_3$—C= <br> \| <br> SCH$_3$ | C$_{12}$H$_{23}$N$_2$O$_5$PS$_3$ | 35.81 | 5.76 | 6.96 | 34.71 | 5.91 | 7.68 |
| CH$_3$—C= <br> \| <br> SC$_2$H$_5$ | C$_{13}$H$_{25}$N$_2$O$_5$PS$_3$ | 37.48 | 6.01 | 6.72 | 36.41 | 6.25 | 7.27 |
| CH$_3$—C= <br> \| <br> SCH$_2$CH$_2$CN | C$_{14}$H$_{24}$N$_3$O$_5$PS$_3$ | 38.07 | 5.48 | 9.52 | 37.03 | 5.89 | 10.01 |
| CH$_3$—C= <br> \| <br> OC$_2$H$_5$ | C$_{13}$H$_{25}$N$_2$O$_5$PS$_2$ | 38.99 | 6.29 | 6.98 | 33.38 | 6.33 | 8.47 |
| CH$_3$—S—C—CH= with O, CH$_3$ substituents | C$_{14}$H$_{27}$N$_2$O$_7$PS$_3$ | 36.34 | 5.88 | 6.05 | 33.60 | 5.76 | 6.42 |
| CH$_3$SCH$_2$C= <br> \| <br> CH$_3$ | C$_{13}$H$_{25}$N$_2$O$_5$PS$_3$ | 37.48 | 6.05 | 6.73 | 37.09 | 6.14 | 7.34 |

TABLE I-continued
ELEMENTAL ANALYSES AND MELTING POINTS OF OXIME N—METHYL-N—(O—ETHYL-S—PROPYL-PHOSPHOROTHIOACETYL)CARBAMATES

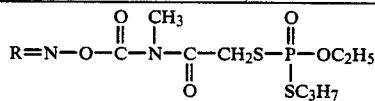

$$R=N-O-\underset{\underset{O}{\|}}{C}-\underset{CH_3}{\overset{|}{N}}-\underset{\underset{O}{\|}}{C}-CH_2S-\underset{SC_3H_7}{\overset{\overset{O}{\|}}{P}}-OC_2H_5$$

| Structure | | Elemental Analysis | | | | | |
|---|---|---|---|---|---|---|---|
| | Molecular | Calculated | | | Found | | |
| R | Formula | C | H | N | C | H | N |
| $(CH_3)_2CHSCH_2-\underset{\underset{CH_3}{\|}}{C}=$ | $C_{15}H_{29}N_2O_5PS_3$ | 40.52 | 6.57 | 6.29 | 40.23 | 7.06 | 6.38 |
| $\underset{CH_3-\overset{\overset{CH_3ON}{\|}}{C}-\underset{\underset{CON(CH_3)_2}{\|}}{C}=}{}$ | $C_{16}H_{29}N_4O_7PS_2$ | 39.65 | 6.03 | 11.56 | 39.50 | 6.39 | 11.79 |
| 4-ylidine-5-methyl-1,3-oxathiolane | $C_{13}H_{23}N_2O_6PS_3$ | 36.26 | 5.38 | 6.50 | 36.08 | 5.56 | 6.38 |
| 2-ylidine-N—methyl-5,5-dimethyl-1,3-thiazolidin-4-one | $C_{15}H_{26}N_3O_6PS_3$ | 38.50 | 5.55 | 9.03 | 38.17 | 5.73 | 8.64 |
| $NC-\underset{\underset{CH_3}{\|}}{\overset{\overset{CH_3}{\|}}{C}}-CH=$ | $C_{14}H_{24}N_3O_5PS_2$ | (Structure confirmed by NMR and IR spectra) | | | | | |

The oxime N-alkyl-N-α-(alkylthiophosphorothio)acylcarbamates of this invention were evaluated to determine their pesticidal activity against selected aphids, mites, worms, beetles and houseflies.

Suspensions of the test compounds were prepared by dissolving 375 mg of compound in 7.5 ml of dimethylformamide. To this was added 15 ml of acetone in which had been dissolved 37.5 mg (10 percent of the weight of the compound) of an alkylphenoxy polyethoxyethanol surfactant, as an emulsifying or dispersing agent. The resulting solution was mixed into 52½ ml of water to give roughly 75 ml of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. Using the test procedures set forth below, pesticidal activity was determined with the results set forth in Table I.

Bean Aphid Foliage Spray Test

Adults and nymphal stages of the bean aphid (*Aphis fabae* Scop.) reared on potted dwarf nasturtium plants at 68°–70° F. and 50±5% relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids were placed on a revolving turntable and sprayed with 100–110 milliliters of test compound formulation by use of a spray gun set at 40 psig air pressure. This application, which lasted 25 seconds, was sufficient to wet the plants to run-off. As a control, 100–110 milliliters of a water-acetone-dimethylformamide-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 68°–70° F. and 50±5 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Mite Foliage Spray Test

Adults and nymphal stage of the two-spotted mite (*Tetranychus urticae* Koch), reared on Tendergreen bean plants at 80±5% relative humidity, were the test organisms. Infested leaves from a stock culture were placed on the primary leaves of two bean plants 6 to 8 inches in height, growing in a 2½ inch clay pot. A sufficient number of mites for testing (150–200) were transferred from the exercised leaves to the fresh plants in a period of 24 hours. Following the 24 hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a spray gun set at 40 psig. air pressure. This application, which lasted 25 seconds, was sufficient to wet the plants to run-off. As a control, 100-110 milliliters of a water solution containing acetone, dimethylformamide and emulsifier in the same concentrations as the test compound formulation, but containing no test compound, were also sprayed on infested plants. The sprayed plants were held at 80±5% relative humidity for 6 days, after which a mortality count of motile forms were made. Microscopic examination for motile forms were made on the leaves of the test plants. Any individual which was capable of locomotion upon prodding was considered living.

Southern Armyworm Leaf Spray Bait Test

Larvae of the southern armyworm (*Spodoptera eridania*, (Cram.)), reared on Seiva Pole lima bean plants at a temperature of 80°±5° F. and a relative humidity of 50±5%, constituted the test insects.

The test compounds were formulated by diluting the stock suspension with water to give a suspension containing 500 parts of test compound per million parts of final formulation. Potted Seiva Pole lima bean plants in the primary leaf stage and of standard height and age were placed on a revolving turntable and sprayed with 100-110 milliliters of test compound formulation by use of a spray gun set at 40 psig air pressure. This application, which lasted 25 seconds, was sufficient to wet plants to run-off. As a control, 100-110 milliliters of water-dimethylformamide-acetone-emulsifer solution containing no test compound were also sprayed on infested plants. When dry, the paired leaves were separated and each one was placed in a 9 centimeter petri dish lined with moistened filter paper. Five randomly selected larvae were introduced into each dish and the dishes were closed. The closed dishes were labeled and held at 80°-85° F. for three days. Although the larvae could easily consume the whole leaf within 24 hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivesti*, Muls.), reared on Seiva Pole lima bean plants at a temperature of 80°±5° F. and 50±5% relative humidity, were the test insects The test compounds were formulated by diluting the stock suspension with water to give a suspension containing 500 parts of test compound per million parts of final formulation. Seiva Pole lima bean plants in the primary leaf stage and of standard height and age were placed on a revolving turntable and sprayed with 100-110 milliliters of test compound formulation by use of a spray gun set at 40 psig air pressure. This application, which lasted 25 seconds, was sufficient to wet plants to run-off. As a control, 100-110 milliliters of a water-dimethylformamide-acetone-emulsifier solution containing no test compound were also sprayed on infested plants. When dry, the paired leaves were separated and each was placed in a 9 centimeter petri dish lined with moistened filter paper. Five randomly selected larvae were introduced into each dish, and the dishes were closed. The closed dishes were labeled and held at a temperature of 80°±5° F., for 3 days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialities, Manufacturing Association (Blue Book, McNair-Dorland Co., N.Y. 1954; pages 243-244, 261) under controlled conditions of 80°±5° F. and 50±5% relative humidity, were the test insects. The flies were immobilized by anesthetizing with carbon dioxide and 25 immobilized individuals, males and females, were transferred to a cage consisting of a standard food strainer about 5 inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the good strainer prior to admitting the anesthetized flies. The caged flies were allowed to feed on the bait for 24 hours, at a temperature of 80°±5° F. and a relative humidity of 50±5%. Flies which showed no sign of movement on prodding were considered dead.

The following Table I, illustrates the broad range of pesticidal activity of the novel compounds of the instant invention. Each compound was assigned a rating based on the following criteria:

A=excellent control at 500 ppm;
B=partial control at 500 ppm;
C=no control at 500 ppm.

It is to be understood that those compounds which gave only partial control or no control for some insects or mites at 500 ppm will exhibit greater control at application levels about 500 ppm.

TABLE II

PESTICIDAL ACTIVITY OF ACYCLIC OXIME N—ALKYL-N—PHOSPHOROTHIOACYLCARBAMATES

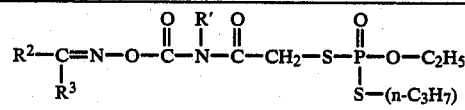

| Compound Number | Structure | | | Biological Activity | | | | |
|---|---|---|---|---|---|---|---|---|
| | R² | R³ | R' | Bean Aphid | Adult Mites | Southern Armyworm | Mexican Bean Beetle | House-fly |
| 1 | methyl | methylthio | methyl | A | A | A | B | A |
| 2 | methyl | methylthio | n-propyl | C | A | A | A | A |
| 3 | methyl | ethylthio | methyl | A | A | A | A | A |
| 4 | methyl | 2-cyanoethylthio | methyl | A | A | A | A | A |
| 5 | methyl | ethoxy | methyl | A | A | A | A | A |
| 6 | 2-methylthio-2-propyl | hydrogen | methyl | A | A | A | A | A |

TABLE II-continued

| | | | | | | | | |
|---|---|---|---|---|---|---|---|---|
| 7 | 2-methylsulfonyl-2-propyl | hydrogen | methyl | A | A | A | A | A |
| 8 | 2-cyano-2-propyl | hydrogen | methyl | A | A | A | A | A |
| 9 | methylthiomethyl | methyl | methyl | A | A | A | A | A |
| 10 | isopropylthiomethyl | methyl | methyl | A | A | A | A | A |
| 11 | N,N—dimethylaminocarbonyl | 1-(1-methyloximinoethyl) | methyl | A | A | B | A | A |

PESTICIDAL ACTIVITY OF CYCLIC OXIME N—ALKYL-N—PHOSPHOROTHIOACYL-CARBAMATES

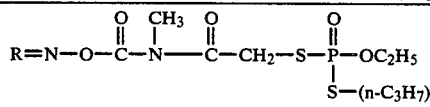

| | | Biological Activity | | | | |
|---|---|---|---|---|---|---|
| Compound Number | Structure R | Bean Aphid | Mites | Southern Armyworm | Mexican Bean Beetle | Housefly |
| 12 | 2-ylidine-1,4-dithiane | A | A | A | A | A |
| 13 | 4-ylidine-5-methyl-1,3-oxathiolane | A | A | A | A | A |
| 14 | 2-ylidine-N—methyl-5,5-dimethyl-1,3-thiazolidin-4-one | B | A | A | A | A |

Insecticidal and miticidal compositions comprising an acceptable and a pesticidally acceptable amount of such compounds can be obtained and applied in methods for controlling insects or mites according to well established procedures. Pesticidal compositions containing such compounds as the active agent will usually comprise a carrier and/or diluent, in either liquid or solid form.

Suitable liquid diluents or carriers include water, petroleum distillates, or other liquid carriers with or without surface active agents. Liquid concentrates can be prepared by dissolving one of these compounds with a nonphytotoxic solvent such as acetone, xylene, or nitrobenzene, followed by dispersing the agents in water with the acids of a suitable surface active, emulsifying and dispersing agents.

The choice of dispersing and emulsifying agents and the amount employed depends on by the nature of the composition and the ability of the agent to facilitate the dispersion of the toxicant. Generally it is desirable to use as little of the agent as is possible, consistent with the desired dispersion of the toxicant in the spray so that rain does not re-emulsify the toxicant after it is applied to the plant and wash it off the plant. Non-ionic, anionic, amphoteric, or cationic dispersing and emulsifying agents may be employed, as for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, betonite, talc, diatomaceous earth, fullers earth, and the like. In the formulation of the wettable powders the aforementioned dispersed agents as well as lignosulfonates can be included.

The required amount of the toxicants contemplated herein can be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides of this invention control the population of insects, mites and mite and insect ova upon plants or other material to which the pesticides are applied. Generally, when used in sufficient amount to kill or repel the insects, they do not burn or injure the plant. The toxicants are compatible with substantially any other constituents of the spray schedule, and they can be used in the soil, upon the seeds, or the roots of plants without injuring either the seeds or roots of plants. They can also be used in combination with other pesticidally active compounds.

I claim:

1. A compound represented by the structural formula:

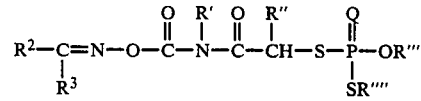

wherein:
Q is oxygen or sulfur;
$R'$ is $C_{1-4}$ alkyl;
$R''$ is hydrogen or $C_{1-4}$ alkyl;
$R'''$ and $R''''$ are individually $C_{1-6}$ alkyl;
$R^2$ is (a) alkyl, cycloalkyl, or phenyl which may be optionally substituted with halogen, alkylsulfinyl, alkylsulfonyl, amido, alkythio, alkoxy, cyano or nitro; or (b) alkanoyl, alkoxy, alkylthio, aminocarbonyl, alkylaminocarbonyl or dialkylaminocarbonyl, provided that $R^2$ may contain no more than six aliphatic carbon atoms; and
$R^3$ is (a) alkyl, alkylthio or alkoxy, all of which may be optionally substituted with cyano, or (b) hydrogen, alkenylthio, alkynylthio, alkoxy or alkyloximino, provided that $R^3$ may contain no more than six carbon atoms.

2. A compound in accordance claim 1 wherein said $R^2$ is $C_{1-4}$ alkyl and said $R^3$ is $C_{1-4}$ alkylthio or $C_{1-4}$ alkoxy.

3. A compound in accordance with claim 1 wherein $R^2$ is methyl, $R'$ is methyl, $R''$ is hydrogen, $R'''$ is ethyl, $R''''$ is n-propyl, Q is oxygen and $R^3$ is methylthio.

4. A compound in accordance with claim 1 wherein $R^2$ is methyl, $R'$ is methyl, $R''$ is hydrogen, $R'''$ is ethyl, $R''''$ is n-propyl, Q is oxygen and $R^3$ is ethylthio.

5. A compound in accordance with claim 1 wherein $R^2$ is methyl, $R'$ is methyl, $R''$ is hydrogen, $R'''$ is ethyl, $R''''$ is n-propyl, Q is oxygen and $R^3$ is 2-cyanoethylthio.

6. A compound in accordance with claim 1 wherein $R^2$ is methyl, $R'$ is methyl, $R''$ is hydrogen, $R'''$ is ethyl, $R''''$ is n-propyl, Q is oxygen and $R^3$ is ethoxy.

7. A compound in accordance with claim 1 wherein $R^3$ is hydrogen, R' is methyl, R" is hydrogen, R'" is ethyl, R"" is n-propyl, Q is oxygen and $R^2$ has the structure:

wherein $R^4$ is $C_{1-4}$ alkylthio, $C_{1-4}$ alkylsulfonyl, cyano, cyanoethyl or nitro.

8. In accordance with claim 1 the compound 2-methylthio-2-methylpropanaldoxime N-methyl-N-(O-ethyl-S-propyl-phosphorothio)acetyl carbamate.

9. In accordance with claim 1 the compound 2-methylsulfonyl-2-methylpropanaldoxime N-methyl-N-(O-ethyl-S-propyl-phosphorothio)acetyl carbamate.

10. In accordance with claim 1 the compound 2-cyano-2-methylpropanaldoxime N-methyl-N-(O-ethyl-S-propyl-phosphorothio)acetyl carbamate.

11. A compound in accordance with claim 1 wherein $R^2$ is isopropylthiomethyl, $R^3$ is methyl, R' is methyl, R" is hydrogen, R'" is ethyl, R"" is n-propyl and Q is oxygen.

12. A compound in accordance with claim 1 wherein $R^3$ is dimethylaminocarbonyl, R' is methyl, R" is hydrogen, R'" is ethyl, R"" is n-propyl, Q is oxygen and $R^2$ has the structure: $-C(CH_3)=N-O-CH_3$.

13. An insecticidal and miticidal composition comprising an acceptable carrier and as the active toxicant a pesticidally effective amount of the pesticidal compound of claim 1.

14. A composition in accordance with claim 13 wherein the active toxicant is a pesticidally effective amount of the compound 1-methylthioacetaldoxime N-methyl-N-(O-ethyl-S-propyl-phosphorothio)acetyl carbamate.

15. A composition in accordance with claim 13 wherein the active toxicant is a pesticidally effective amount of the compound 2-methyl-2-cyanopropanaldoxime N-methyl-N-(O-ethyl-S-propylphosphorothio)acetyl carbamate.

16. A method for controlling insects or mites comprised of subjecting them to a pesticidally effective amount of the compound of claim 1.

17. The method of claim 16 wherein the pesticidal compound is the compound 1-methylthioacetaldoxime N-methyl-N-(O-ethyl-S-propyl-phosphorothio)acetyl carbamate.

18. The method of claim 16 wherein the pesticidal compound is the compound 2-methyl-2-cyanopropanaldoxime N-methyl-N-(O-ethyl-S-propyl-phosphorothio)acetyl carbamate.

* * * * *